United States Patent
Kim et al.

(10) Patent No.: US 11,419,692 B2
(45) Date of Patent: Aug. 23, 2022

(54) ARTICULATING STRUCTURE USING ROLLING JOINT AND PIN COUPLING, AND TUBE INSERT DEVICE HAVING THE SAME

(71) Applicant: KOREA INSTITUTE OF SCIENCE AND TECHNOLOGY, Seoul (KR)

(72) Inventors: Keri Kim, Seoul (KR); Jeongryul Kim, Seoul (KR); Seong Il Kwon, Seoul (KR)

(73) Assignee: KOREA INSTITUTE OF SCIENCE AND TECHNOLOGY, Seoul (KR)

(*) Notice: Subject to any disclaimer, the term of this patent is extended or adjusted under 35 U.S.C. 154(b) by 144 days.

(21) Appl. No.: 16/711,430

(22) Filed: Dec. 12, 2019

(65) Prior Publication Data
US 2020/0323599 A1    Oct. 15, 2020

(30) Foreign Application Priority Data
Apr. 9, 2019    (KR) .......................... 10-2019-0041382

(51) Int. Cl.
*A61B 34/00*    (2016.01)
(52) U.S. Cl.
CPC .................................... *A61B 34/71* (2016.02)
(58) Field of Classification Search
CPC ............. A61B 34/71; A61B 1/008; A61B 2017/00323; B25J 9/106; B25J 17/025; B25J 9/065
See application file for complete search history.

(56) References Cited

U.S. PATENT DOCUMENTS

| 4,834,069 A * | 5/1989 | Umeda ................ A61B 1/0055 138/120 |
| 6,817,974 B2 | 11/2004 | Cooper et al. |
| 8,893,749 B2 * | 11/2014 | Perry .................. A61B 1/0055 138/120 |

(Continued)

FOREIGN PATENT DOCUMENTS

| KR | 101180820 B1 | 9/2012 |
| KR | 1020130132233 A | 12/2013 |

(Continued)

OTHER PUBLICATIONS

Yong-Jae Kim et al. "A Stiffness-Adjustable Hyperredundant Manipulator Using a Variable Neutral-Line Mechanism for Minimally Invasive Surgery," IEEE Transactions on Robotics, Apr. 2014, pp. 382-395, vol. 30, No. 2.

*Primary Examiner* — Bobby Rushing, Jr.
(74) *Attorney, Agent, or Firm* — Cantor Colburn LLP

(57) ABSTRACT

There is disclosed an articulating structure that is steered by relative movement of a plurality of segments connected in series, the articulating structure including a first segment and a second segment arranged in contact with each other, wherein contact surfaces of the first segment and the second segment are rolling contact surfaces in line contact on a first direction contact line, the first segment has a pin on a side, the second segment has a coupling hole into which the pin is inserted, the first segment and the second segment make a relative rolling movement for translation of the first direction contact line while maintaining the line contact, and the coupling hole is formed with a larger area than the pin to allow the pin to make a relative position movement within the coupling hole during the rolling movement.

14 Claims, 11 Drawing Sheets

(56) References Cited

U.S. PATENT DOCUMENTS

| | | | |
|---|---|---|---|
| 9,572,628 B2* | 2/2017 | Zubiate | ................ A61B 34/30 |
| 9,833,290 B2 | 12/2017 | Jeong et al. | |
| 2013/0312564 A1 | 11/2013 | Kim et al. | |
| 2018/0125596 A1 | 5/2018 | He et al. | |

FOREIGN PATENT DOCUMENTS

| | | | | |
|---|---|---|---|---|
| KR | 101427322 B1 | 8/2014 | | |
| WO | WO-2008045394 A2 * | 4/2008 | ......... | A61B 17/0469 |

* cited by examiner

ARTICULATING STRUCTURE USING ROLLING JOINT AND PIN COUPLING, AND TUBE INSERT DEVICE HAVING THE SAME

CROSS-REFERENCE TO RELATED APPLICATION

This application claims priority to Korean Patent Application No. 10-2019-0041382, filed on Apr. 9, 2019, and all the benefits accruing therefrom under 35 U.S.C. § 119, the contents of which in its entirety are herein incorporated by reference.

BACKGROUND

1. Field

The present disclosure relates to an articulating structure and a tube insert device having the same, and more particularly, to an articulating structure using both rolling joint and pin coupling and a tube insert device having the same.

Description of Government-Funded Research and Development

This research is conducted by Hanyang Digitech, and funded by robotics industry core technology development (R&D) of Korea Evaluation Institute of Industrial Technology, Ministry of Trade, Industry and Energy, Republic of Korea (Development of flexible joint single passage surgical robotic technology based on fluoroscopy-induced endoscopy for transoral and laparoscopic surgery, No. 1415158632).

2. Description of the Related Art

A typical example of a tube insert device used to perform a predetermined operation by inserting a long hollow tube into a narrow space is microsurgical instruments for minimally invasive surgery.

The minimally invasive surgery is a surgery that is performed through a minimal incision as compared to open surgery, and it has advantages such as small incisions, less or no scars or after effects and fast recovery.

The microsurgical instruments for minimally invasive surgery are used to perform a predetermined operation such as surgery in a narrow space, so its control has been studied so much.

Particularly, suggests have been various types of articulating structures for locally changing the direction of an end effector positioned at the front end of the microsurgical instrument.

It is known that the articulating structure typically has a structure in which a plurality of segments is connected in series, and steering is accomplished by the relative movements of adjacent segments.

The plurality of segments is generally fixed in place with respect to each other by pulling using a steering means, for example, a wire, but when the segments are only supported by the wire without any other fixing means, the segments may be separated by an unexpected external force.

Accordingly, as in U.S. Pat. No. 9,833,290, for example, a structure of fixing each segment using pin coupling is employed. In U.S. Pat. No. 9,833,290, pin coupling serves as a hinge that is the center of pivot in the relative movements of the segments.

The two segments supported by the fixed pin cannot smoothly move due to loads focused on the pin during movements.

Moreover, to install the pin coupling, a gap is formed between the two segments, and thus the entire length of the articulating structure increases and stiffness of the articulating structure against bending loads reduces as much.

Furthermore, when the pin coupling serves as a hinge, a passage along which a wire passes through the segments is significantly misaligned when bending, causing a so-called "caught" wire phenomenon, which hinders the precise control of the articulating structure.

SUMMARY

The present disclosure is designed to solve the above-described problem, and therefore the present disclosure is directed to providing an articulating joint for allowing smooth and precise steering and maintaining tight coupling between a plurality of segments and a tube insert device having the same.

To achieve the above-described object, according to an aspect of the present disclosure, there is provided an articulating structure that is steered by relative movement of a plurality of segments connected in series, the articulating structure including a first segment and a second segment arranged in contact with each other, wherein contact surfaces of the first segment and the second segment are rolling contact surfaces in line contact on a contact line ("a first direction contact line") extending in a first direction, the first segment has a pin on a side, the second segment has a coupling hole into which the pin is inserted, the first segment and the second segment make a relative rolling movement for translation of the first direction contact line while maintaining the line contact, and the coupling hole is formed with a larger area than the pin to allow the pin to make a relative position movement within the coupling hole during the rolling movement.

According to an embodiment, the coupling hole may be formed to allow the pin to be relatively far away from the second segment during the rolling movement.

According to an embodiment, the coupling hole may include an inner side where the pin makes a relative position movement while being in contact during the rolling movement, and the inner side may include an inner side formed at an angle such that a width of the first direction of the coupling hole increases as it far away from the rolling contact surface of the second segment.

According to an embodiment, the pin may make a position movement in contact with the inner side, and the inner side of the coupling hole may be formed in a curved shape.

According to an embodiment, the pin may be positioned close to an upper end portion of the side of the first segment.

According to an embodiment, the pin may protrude from the side of the first segment, the side of the first segment may include a curved part and a flat part along a circumferential direction of the side of the first segment, the flat part may extend in a second direction perpendicular to the first direction, and the pin may be formed in the flat part.

According to an embodiment, the curved part may be formed as part of a circumference of a circular cylinder, and when a circumference of a perfect circular cylinder is defined by extending the curved part, a height of the pin may not go beyond the circumference of the perfect circular cylinder.

According to an embodiment, the second segment may include a flange extending toward the first segment and having the coupling hole, and the flange may cover at least a portion of the flat part and have an inner surface parallel to a surface of the flat part.

According to an embodiment, the entire rolling contact surface of the first segment and the second segment may be formed as part of a circumference of a circular cylinder.

According to an embodiment, the articulating structure may include a third segment positioned in contact with the second segment, contact surfaces of the second segment and the third segment may be rolling contact surfaces in line contact with each other on a contact line ("a second direction contact line") extending in a second direction perpendicular to the first direction, the second segment may have a pin on a side, the third segment may have a coupling hole into which the pin formed in the second segment is inserted, and the second segment and the third segment may make a relative rolling movement for translation of the second direction contact line while maintaining the line contact.

According to an embodiment, the plurality of segments may have a wire connection hole passing through each segment in a front-rear direction, when the articulating structure is placed in a straight line, a wire may pass through the wire connection holes of each segment arranged such that the wire connection holes are aligned in a lengthwise direction of the articulating structure, and the plurality of segments may make the relative movement by pulling or releasing the wire in the lengthwise direction of the articulating structure.

According to an embodiment, the wire connection holes may include a pair of first direction wire connection holes arranged in the first direction and a pair of second direction wire connection holes arranged in the second direction.

According to an embodiment, a tool connection hole passing through each segment in the front-rear direction may be formed at a center of the plurality of segments.

According to another aspect of the present disclosure, there is provided a tube insert device including an elongated tube, and the articulating structure connected to a front end of the tube.

DETAILED DESCRIPTION

Figure 1:
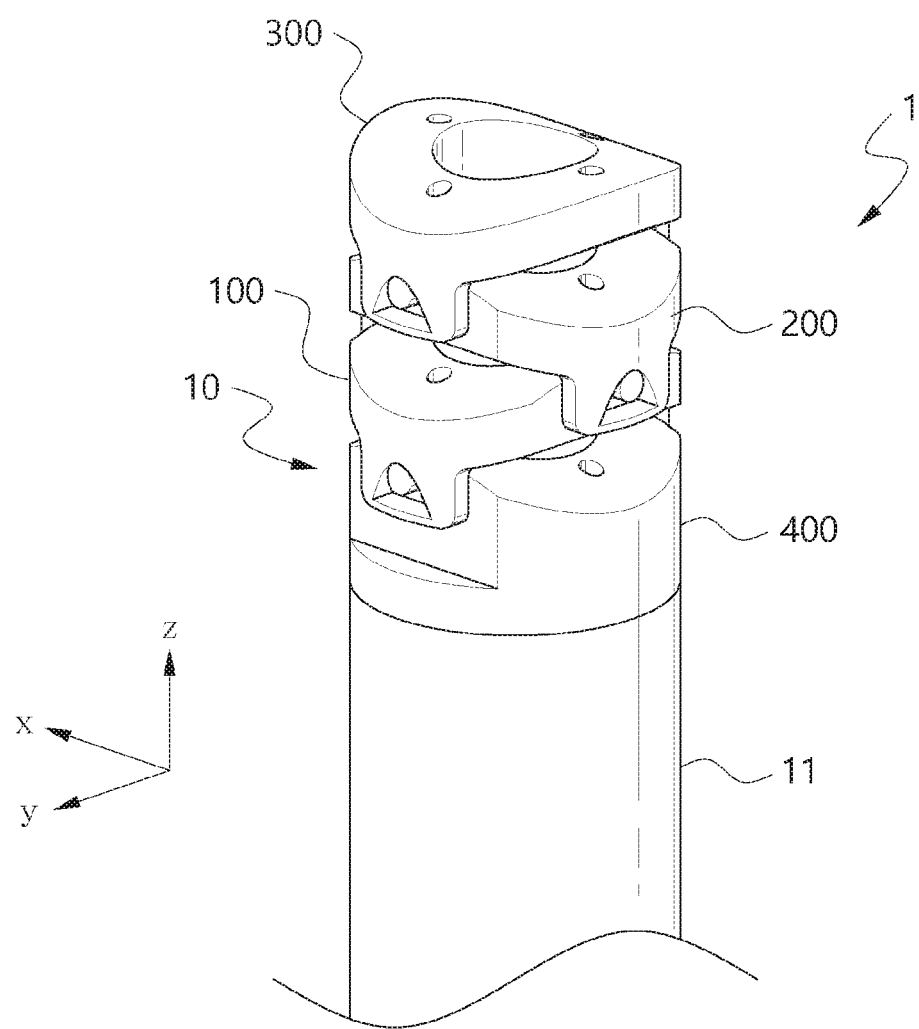
FIG. 1 is a perspective view of a surgical instrument having an articulating structure according to an embodiment of the present disclosure.

Hereinafter, exemplary embodiments of the present disclosure will be described with reference to the accompanying drawings. The present disclosure is described with reference to the embodiments shown in the drawings, but this is described as one embodiment, and the technical spirit of the present disclosure and its essential elements and operation are not limited thereto.

FIG. 1 is a perspective view of a surgical instrument 1 having an articulating structure 10 according to an embodiment of the present disclosure.

As shown in FIG. 1, the articulating structure 10 includes a plurality of segments 100, 200, 300, 400 connected in series. As described below, the articulating structure 10 has a structure such that it is steered by the bending by relative movements of the plurality of segments 100, 200, 300, 400.

According to this embodiment, for example, the articulating structure 10 is used as an end effector of the tube insert device 1.

For example, the tube insert device 1 is a microsurgical instrument that is inserted into the body to perform various types of surgeries, and includes a tube 11 that extends longitudinally to be inserted into the body, and the articulating structure 10 according to this embodiment is attached to the front end. However, the tube insert device 1 according to this embodiment is not limited to a microsurgical instrument, and may be used in various types of tasks requiring a tube that is so thin and long as to be inserted into a narrow orifice.

The articulating structure 10 makes bending movements at the front end of the tube 11 to allow stable steering of the tip of the tube insert device 1 in all directions with high curvature, thereby enhancing the stability and convenience of the non-invasive surgery.

As shown in FIG. 1, the articulating structure 10 includes a proximal segment (a fourth segment) 400, a first segment 100 positioned in series in contact with the fourth segment 400, a second segment 200 positioned in series in contact with the first segment 100, and a distal segment (a third segment) 300 positioned in series in contact with the second segment 200.

In the specification, when the first to fourth segments 100 to 400 are arranged in a straight line, a direction of a line connecting the centers of the first to fourth segments 100 to 400 is defined as a lengthwise direction Z of the articulating structure 10.

Figure 2A:
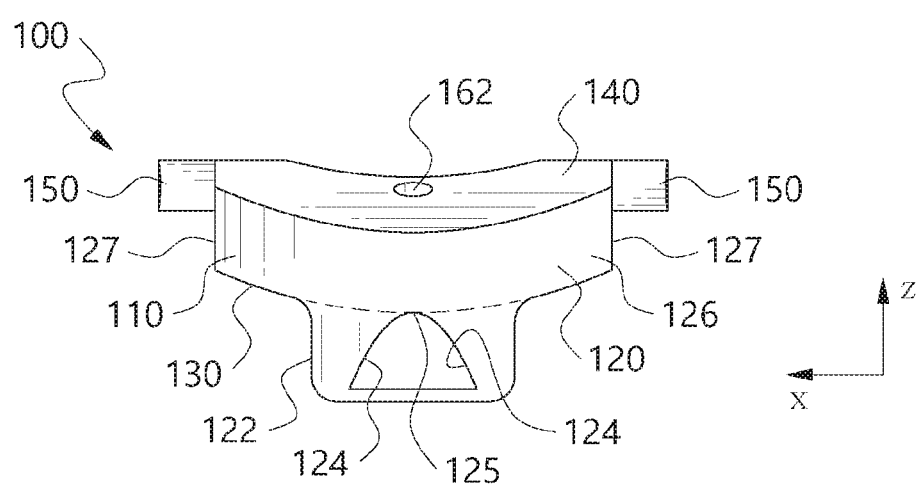
FIGS. 2A to 2C are diagrams showing a first segment of an articulating structure.
Figure 2B:
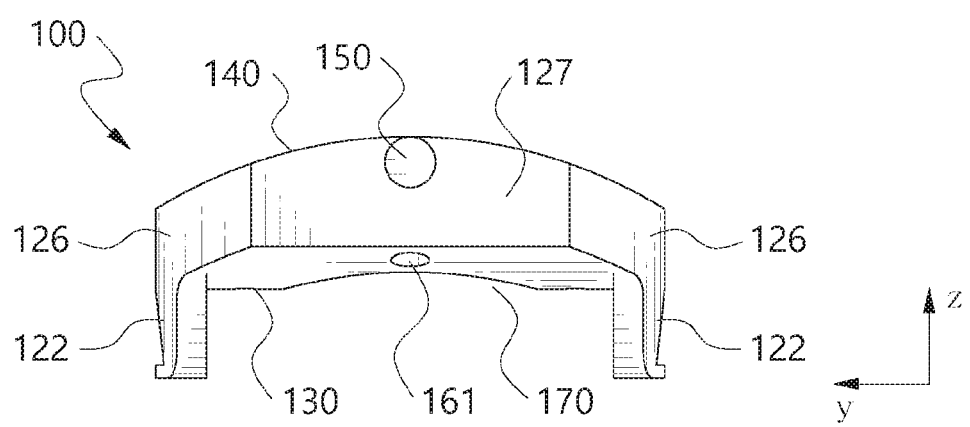
Figure 2C:
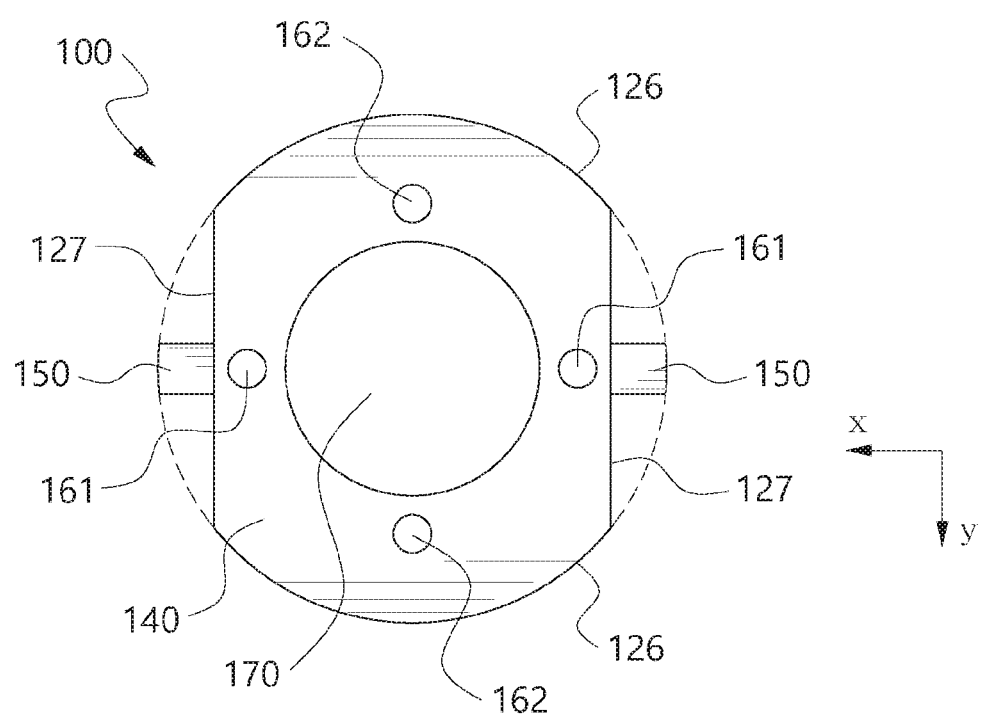

FIGS. 2A to 2C are diagrams showing the first segment 100 of the articulating structure 10. FIG. 2A is a front view of the first segment 100, FIG. 2B is a side view of the first segment 100, and FIG. 2C is a plane view of the first segment 100.

As shown in FIGS. 2A to 2C, the first segment 100 includes a body 110 having a predetermined thickness, two pins 150 formed on a side 120 of the body 110, and two flanges 122 formed on the side 120 of the body 110.

The body 110 has a first front rolling contact surface 140 on the front side, and a first rear rolling contact surface 130 on the rear side.

In this embodiment, "front" indicates a distal direction of the articulating structure 10, and "rear" indicates a proximal direction of the articulating structure 10. When the articulating structure 10 is placed in a straight line, the front-rear direction of each segment match the lengthwise direction Z of the articulating structure 10. However, "front" and "rear" are relative terms, and on the contrary, when the distal side of the articulating structure 10 is defined as "rear", the proximal side is defined as "front".

As clearly shown in FIG. 2B, according to this embodiment, the first front rolling contact surface 140 is part of the circumference of a circular cylinder around an imaginary axis line extending in a first direction X, spaced apart a predetermined distance in the rear direction from the first front rolling contact surface 140.

Also, as clearly shown in FIG. 2A, according to this embodiment, the first rear rolling contact surface 130 is part of the circumference of a circular cylinder around an imaginary axis line extending in a second direction Y, spaced apart a predetermined distance in the front direction from the first rear rolling contact surface 130.

That is, the first front rolling contact surface 140 and the first rear rolling contact surface 130 are arranged by 90°.

As shown in FIG. 2C, the side 120 of the body 110 has two curved parts 126 and two flat parts 127 in an alternating manner along the circumferential direction of the side 120.

The two curved parts 126 are formed by part of the circumference of a circular cylinder around a central axis line of the front-rear direction of the articulating structure 10. Accordingly, as shown in FIG. 2C, the circumference of a perfect circular cylinder (see the dash line) may be defined by extending the curved parts 126.

The two flat parts 127 are flat surfaces parallel to each other, and extend along the second direction Y.

The flat parts 127 each has the two pins 150. The pins 150 extend in the first direction X.

According to this embodiment, when the circumference of the perfect circular cylinder is defined by extending the curved parts 126, the heights of the pins 150 do not go beyond the circumference of the perfect circular cylinder. Additionally, the pins 150 are positioned close to the upper end portions of the flat parts 127. According to this embodiment, as shown in FIG. 2B, when the first segment 100 is viewed from the side, the pins 150 form a circle that contacts the first front rolling contact surface 140. That is, the positions of the front-rear direction of the top of the pins 150 approximately match the first front rolling contact surface 140.

Here, the pin 150 may be integrally formed with the flat part 127. However, according to this embodiment, for the convenience of assembly of the articulating structure 10, a through-hole (not shown) is formed in the flat part 127, and the pin 150 is installed in the first segment 100 by insert coupling of the pin 150 into the corresponding through-hole.

The two curved parts 126 each has the flanges 122 extending rearward. That is, the two flanges 122 are arranged in the second direction Y.

According to this embodiment, the flange 122 is formed in the shape of an approximately rectangular plate. According to this embodiment, the outer surface of the flange 122 is a curved surface smoothly connected to the curved part 126, and is formed as part of the circumference of the circular cylinder defined by the curved part 126. In contrast, the inner surface of the flange 122 is formed by a flat surface extending along the first direction X.

The flange 122 has a coupling hole 123 passing therethrough in the second direction Y. According to this embodiment, the coupling hole 123 is a hole of an approximately triangular shape having a height in the front-rear direction and a width in the first direction X.

The coupling hole 123 includes two inner sides 124 that define the width of the coupling hole 123. The two inner sides 124 are inclined to form a vertex 125 toward the rolling contact surfaces 130, 140. That is, the two inner sides 124 are formed such that the width of the coupling hole 123 increases as it is far away from the rolling contact surfaces 130, 140 of the first segment 100.

The two inner sides 124 are formed as gently curved surfaces, and smoothly reach the vertex 125. A curved surface having a curvature that is equal to or larger than the curvature of the pin 150 is formed around the vertex 125 at which the two sides 124 meet.

According to this embodiment, as shown in FIG. 2A, when the first segment 100 is viewed from the side, the vertex 125 of the coupling hole 123 is in contact with the first rear rolling contact surface 130. That is, the positions of the front-rear direction of the top of the vertices 125 of the coupling holes 123 approximately match the first rear rolling contact surface 130.

The body 110 has a plurality of wire connection holes 161, 162 passing through the body 110 in the front-rear direction. According to this embodiment, the body 110 has four wire connection holes 161, 162, and the wire connection holes 161, 162 include a pair of first direction wire connection holes 161 arranged in the first direction X and a pair of second direction wire connection holes 162 arranged in the second direction Y.

As shown in FIG. 2C, the pair of first direction wire connection holes 161 are disposed on an approximately straight line with the two pins 150, and the pair of second direction wire connection holes 162 are arranged in approximately 90° rotation relative to the first direction wire connection holes 161 when viewed in the plane.

A tool connection hole 170 passing through the body 110 in the front-rear direction is formed at the center of the first segment 100 surrounded by the four wire connection holes 161, 162.

The first segment 100 configured as described above is positioned in contact with the second segment 200 in the front-rear direction, and they are coupled to each other.

According to this embodiment, the configuration of the second segment 200 is substantially the same as the first segment 100. The second segment 200 is described by replacing some letters and numbers used in FIGS. 2A to 2C and the above description of FIGS. 2A to 2C, such as "first" with "second", 100 and subsequent numbers with 200 and subsequent numbers, the first direction X with the second direction Y, and the second direction Y with the first direction Y. Accordingly, in the description of the configuration of the second segment 200, redundant descriptions are omitted herein.

Figure 3:
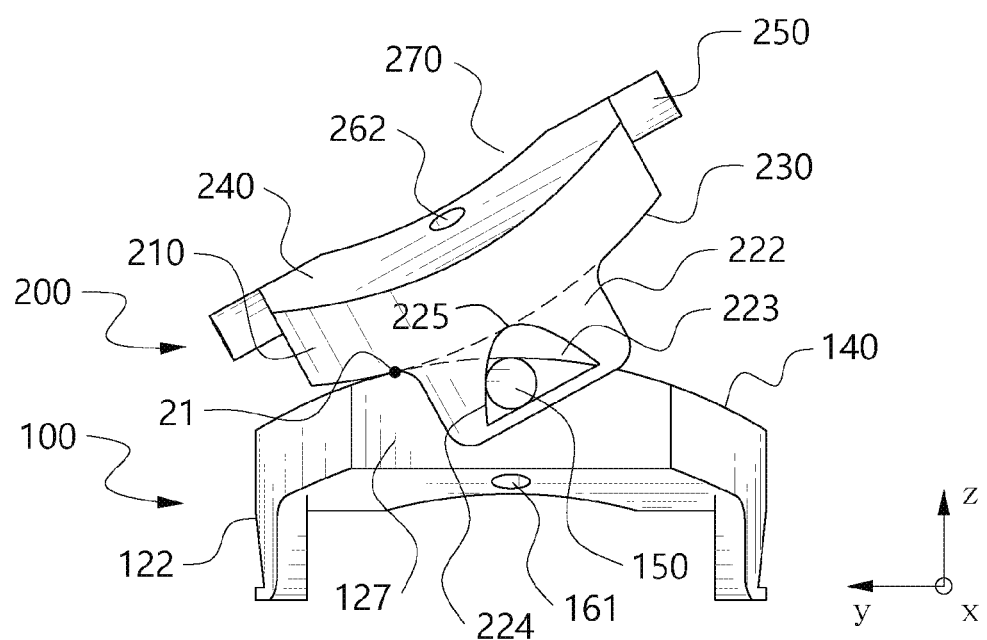
FIG. 3 is an assembled state diagram of a first segment and a second segment of an articulating structure.

FIG. 3 shows the first segment 100 and the second segment 200 coupled to each other.

As shown in FIG. 3, the first segment 100 and the second segment 200 arranged in the front-rear direction are connected to bring the first front rolling contact surface 140 of the first segment 100 and a second rear rolling contact surface 230 of the second segment into contact with each other.

As described above, the first front rolling contact surface 140 is part of the circumference of the circular cylinder having the center axis on the rear side, and the second rear rolling contact surface 230 is part of the circumference of the circular cylinder having the center axis on the front side, and thus the contact surfaces (the first front rolling contact surface 140 and the second rear rolling contact surface 230) between the first segment 100 and the second segment 200 are in line contact with each other on a contact line ("a first direction contact line") 21 extending in the first direction X.

When the first front rolling contact surface 140 and the second rear rolling contact surface 230 are in contact with each other, a flange 222 of the second segment 200 extends such that it covers at least some of the flat part 127 of the side 120 of the first segment 100.

Accordingly, a coupling hole 223 of the second segment 200 is disposed on the flat part 127 of the first segment 100. When the coupling hole 223 of the second segment 200 is disposed on the flat part 127 of the first segment 100, the pin 150 of the first segment 100 is inserted into the coupling hole 223 of the second segment 200 by insert coupling of the pin 150 into the flat part 127 of the first segment 100. Accordingly, the two segments 100, 200 are coupled by pin coupling.

When the first segment 100 and the second segment 200 are arranged in a straight line without relative bending, forming the first direction contact line 21 at the center of the first front rolling contact surface 140 and the second rear rolling contact surface 230 (initial state), the pin 150 of the first segment 100 is disposed on the top of the coupling hole 223 of the second segment 200 (see FIG. 1).

As described above, a curved surface that is equal to or larger than the curvature of the pin 150 is formed around a vertex 225 of the coupling hole 223. Accordingly, the pin 150 of the first segment 100 is disposed in contact with the vertex 225 of the coupling hole 223 of the second segment 200.

Additionally, the positions of the front-rear direction Z of the top of the pins 150 approximately match the first front rolling contact surface 140, and the positions of the front-rear direction Z of the vertices 225 of the coupling holes 223 approximately match the second rear rolling contact surface 230, and thus when the pins 150 are disposed at the vertices 225 of the coupling holes 223, the first front rolling contact surface 140 and the second rear rolling contact surface 230 can maintain their contact.

As shown in FIG. 3, according to this embodiment, as described below, when a force is applied to one side of the second segment 200 by a driving means such as a wire, the first segment 100 and the second segment 200 make relative rolling movements, and accordingly the second segment 200 is slanted with respect to the first segment 100. In this instance, the two segments 100, 200 make rolling movements with the translation of the first direction contact line 21 in approximately the second direction Y while maintaining the line contact.

As described above, the articulating structure 10 bends by relative rolling movements between adjacent segments in line contact with each other, thereby minimizing the contact area between the segments of the joint and dissipating loads at the contact point, hence allowing smooth and high curvature bending movements with a small force. Additionally, as the contact between the two segments 100, 200 is maintained, the entire length of the articulating structure 10 reduces.

According to this embodiment, the first front rolling contact surface 140 of the first segment 100 and the second rear rolling contact surface 230 of the second segment 200 in contact with each other are formed such that the entire corresponding surface is part of the circumference of the circular cylinder. Accordingly, it is possible to minimize an area irrelevant to rolling movement, thereby reducing the diameter of the articulating structure 10. However, when not only a central tool connection hole 570 but also an additional auxiliary tool connection hole is formed, the first front rolling contact surface 140 and the second rear rolling contact surface 230 may be part of the front surface of the first segment 100 and the rear surface of the second segment 200 respectively.

Additionally, according to this embodiment, the first front rolling contact surface 140 of the first segment 100 and the second rear rolling contact surface 230 of the second segment 200 are part of the circumference of the circular cylinders having the same radius (that is to say, the curvature of the first front rolling contact surface 140 is equal to the curvature of the second segment 200). Accordingly, it is possible to simplify the computation for steering control of the articulating structure 10.

Meanwhile, according to this embodiment, the coupling hole 223 of the second segment 200 is formed with a larger area than the pin 150 of the first segment 100. Accordingly, as shown in FIG. 3, during relative rolling movements of the first segment 100 and the second segment 200, the pin 150 can make relative position movements within the coupling hole 223.

According to this embodiment, the coupling hole 223 has a height in the front-rear direction, so that the pin 150 is relatively far away from the second segment 200 during rolling movements.

For example, the coupling hole 223 may be formed linearly in the lengthwise direction of the second segment 200, but according to this embodiment, the inner side 224 is formed at an angle such that the width of the coupling hole 223 increases as it is far away from the second rear rolling contact surface 230 of the second segment 200. Accordingly, when the two segments 100, 200 make relative rolling movements, the pin 150 of the first segment 100 may move to the rear side of the second segment 200 within the coupling hole 223 of the second segment 200, and at the same time, make relative position movements in the widthwise direction of the coupling hole 223 from the vertex 225.

In this instance, the pin 150 makes relative movements along the inner side 224 while being in contact with the inner side 224 of the coupling hole 223. According to this embodiment, the inner side 224 is formed as a gently curved surface to help the smooth rolling movements of the two segments 100, 200.

As the coupling hole 223 has an approximately triangular shape by the inclined inner sides 224, when the second segment 200 is slanted at a predetermined angle with respect to the first segment 100, as shown in FIG. 3, the pin 150 comes into contact with two surfaces that form an edge of one side of the coupling hole 223. Accordingly, relative movements of the pin 150 in the same direction within the coupling hole 223 are hindered, and the second segment 200 cannot be slanted with respect to the first segment 100 any longer. That is, the edge of the coupling hole 223 acts as a sort of stopper. The maximum bending angle of the articulating structure 10 may be adjusted by adjusting the angle and width of the edge of the coupling hole 223.

According to this embodiment, relative position movements of the pin 150 within the coupling hole 223 are allowed, thereby allowing the first segment 100 and the second segment 200 to make relative rolling movements while maintaining the line contact, and preventing the unexpected disconnection and separation of the first segment 100 and the second segment 200 in the front-rear direction and the second direction Y by the connection relationship between the pin 150 and the coupling hole 223.

Additionally, according to this embodiment, as the flanges 222 of the second segment 200 having the coupling holes 223 cover and support the side 127 of the first segment 100 on two sides of the first direction X, it is possible to prevent the first segment 100 and the second segment 200 from being dislocated or separated in the first direction X during rolling movements.

Accordingly, the articulating structure 10 has the rolling joint having a smooth moving characteristic and may maintain the stiffness of the joint by pin coupling.

Additionally, according to this embodiment, as the pin 150 makes relative position movements in the widthwise direction of the coupling hole 223 from the vertex 225 within the coupling hole 223, the second segment 200 may be slanted at a larger angle with respect to the first segment 100.

According to the connection of the first segment 100 and the second segment 200 as described above, the articulating structure 10 may bend in the second direction Y.

According to this embodiment, to provide a 2 degree of freedom to the articulating structure 10, the third segment 300 is additionally connected to the second segment 200.

Figure 4:
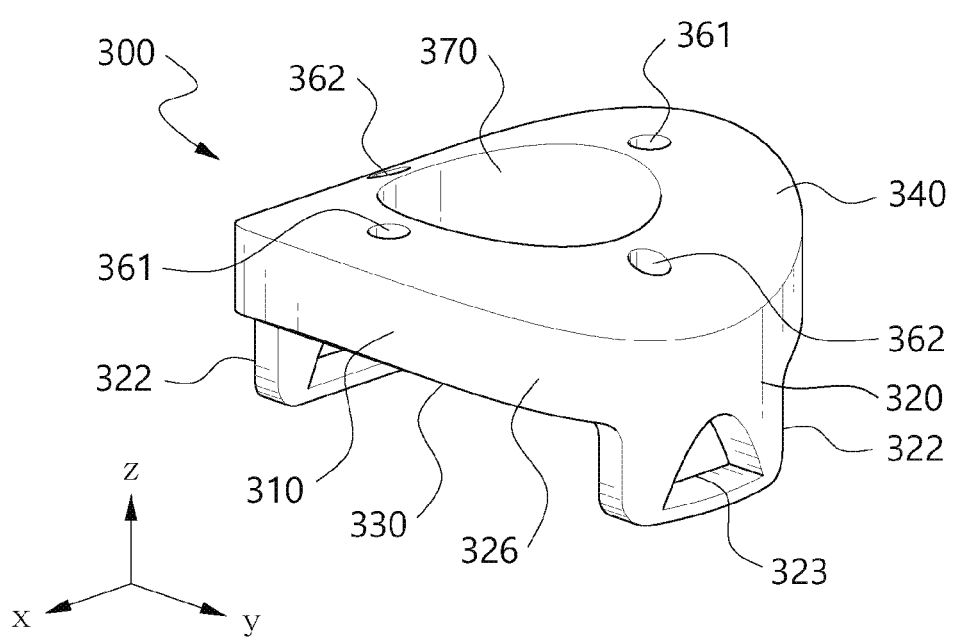
FIG. 4 is a perspective view of a third segment of an articulating structure.

FIG. 4 is a perspective view of the third segment 300.

As shown in FIGS. 1 and 4, the third segment 300 is a distal segment disposed at the most distal position of the articulating structure 10.

Referring to FIG. 4, the third segment 300 according to this embodiment has the same configuration as the first segment 100 except that a side 320 of a body 310 forms a circumference of a perfect circular cylinder by a curved part 326 and thus does not have a flat part, and does not have a pin to be formed in the flat part. Here, although a front surface of the third segment 300 is a third front rolling contact surface 340 that forms part of the circumference of the circular cylinder, the front surface of the third segment 300, namely, the most distal surface of the articulating structure 10 may be formed as a flat surface.

As shown in FIG. 1, the third segment 300 is positioned in contact with the second segment 200 on the front side of the second segment 200. In this instance, a second front rolling contact surface 240 of the second segment 200 and a third rear rolling contact surface 330 of the third segment 300 contact each other, and the second front rolling contact surface 240 and the third rear rolling contact surface 330 are in line contact on a contact line ("a second direction contact line") 22 extending in the second direction Y (see FIGS. 6 and 8).

A pin 250 of the second segment 200 is inserted into a coupling hole 323 formed in a flange 322 of the third segment 300.

The second segment 200 and the third segment 300 connected as described above make relative rolling movements in the first direction X with the translation of the second direction contact line 22 while maintaining the line contact. The movement of the second segment 200 and the third segment 300 will be described in more detail below.

Although this embodiment shows a distal segment forming the distal side of the articulating structure 10 as the third segment 300 connected to the second segment 200, the present disclosure is not limited thereto. The third segment 300 may have perfectly the same structure as the first segment 100. In this case, segments of the same structure as the second segment 200 may be further connected to the front side of the third segment 300. That is, the articulating structure 10 according to this embodiment may increase the length as much as desired by connecting the segments of the same structure as the first segment 100 to the front side of the first segment 100 one after another by 90°.

Figure 5:
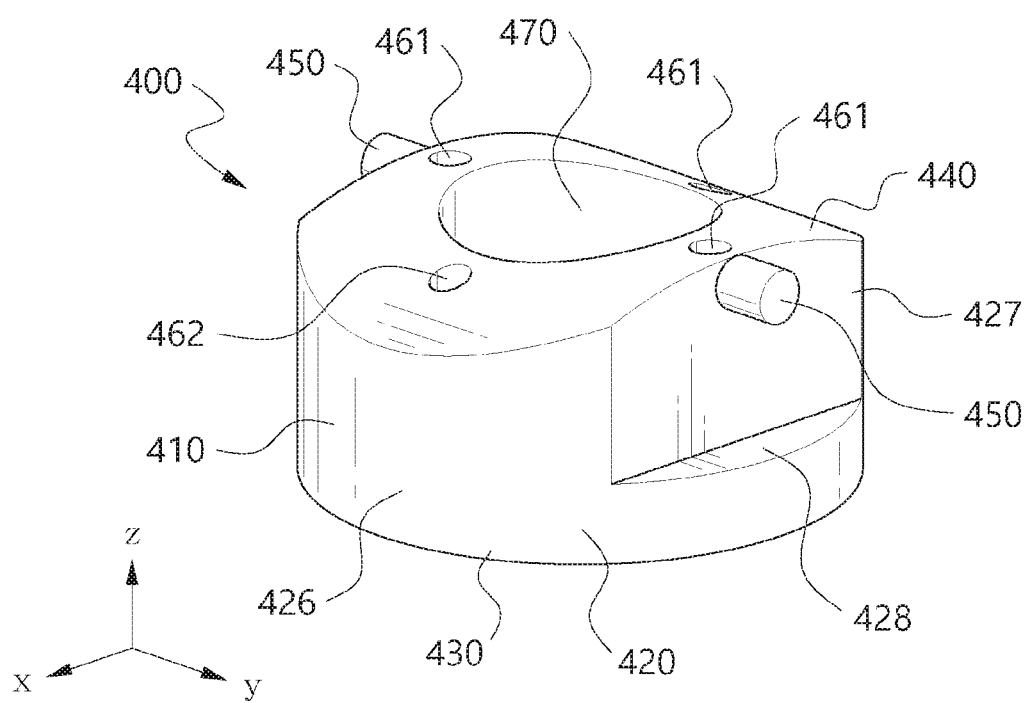
FIG. 5 is a perspective view of a fourth segment of an articulating structure.

Alternatively, other segment may be connected to the rear side of the first segment 100. FIG. 5 is a perspective view of the fourth segment 400 connected to the rear side of the first segment 100.

As shown in FIGS. 1 and 5, the fourth segment 400 is a proximal segment disposed at the most proximal position of the articulating structure 10.

Referring to FIG. 5, the fourth segment 400 according to this embodiment basically has similar configuration to the second segment 200. However, the fourth segment 400 includes a body 410 having a slight larger thickness than the other segments, a curved part 426 extends rearward of a flat part 427 of a side 420, forming a step 428, and a rear surface 430 is flat, and thus a rear rolling contact surface is not formed. Accordingly, it is easy to couple to the front end of the cylindrical tube 11.

As shown in FIG. 1, the fourth segment 400 is positioned in contact with the first segment 100 on the rear side of the first segment 100. In this instance, the first rear rolling contact surface 130 of the first segment 100 and a fourth front rolling contact surface 440 of the fourth segment 400 contact each other, and the first rear rolling contact surface 130 and the fourth front rolling contact surface 440 are in line contact with each other on the second direction contact line 22 (see FIGS. 6 and 8). A pin 450 of the fourth segment 400 is inserted into the coupling hole 123 of the first segment 100.

In the same way as the second segment 200 and the third segment 300, the first segment 100 and the fourth segment 400 connected as described above make rolling movements in the first direction X with the translation of the second direction contact line 22 while maintaining the line contact. The movements of the first segment 100 and the fourth segment 400 will be also described in more detail below.

Likewise, instead of the fourth segment 400, the articulating structure 10 may increase the length as much as desired by connecting segments of the same structure to the first segment 100 to the rear side of the first segment 100 one after another by 90°.

The articulating structure 10 according to this embodiment has pins on the side of each segment, and further, places the pins close to the upper end portion of the side of the segment, thereby minimizing the height of each segment.

Accordingly, it is possible to design a more compact structure of the articulating structure 10.

Further, according to this embodiment, flat parts are installed on the side of each segment, and the pins are installed in the flat parts such that the pins do not protrude out of a circle formed by curved parts of the side (see FIG. 2C). Accordingly, any element does not protrude out of the boundary of the circle defined by the segment when the articulating structure 10 is viewed in the lengthwise direction Z. Accordingly, as the pins are formed on the side of the segment, it is possible to prevent an increase in the diameter of the articulating structure 10.

Hereinafter, the steering operation of the articulating structure 10 configured as described above will be described with reference to FIGS. 6 to 9.

Figure 6:
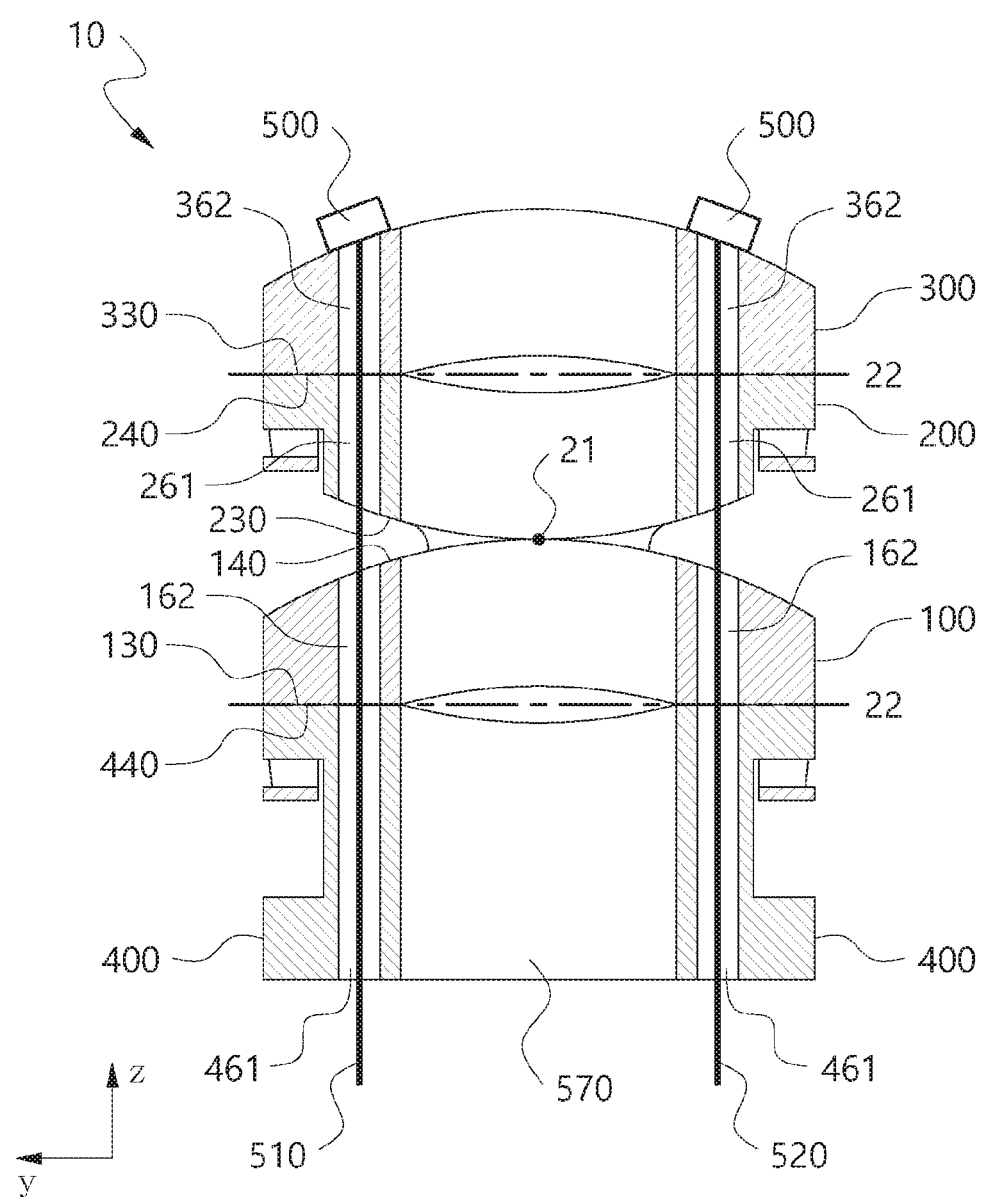
FIG. 6 is a cross-sectional view of an articulating structure when viewed from a first direction.
Figure 7:
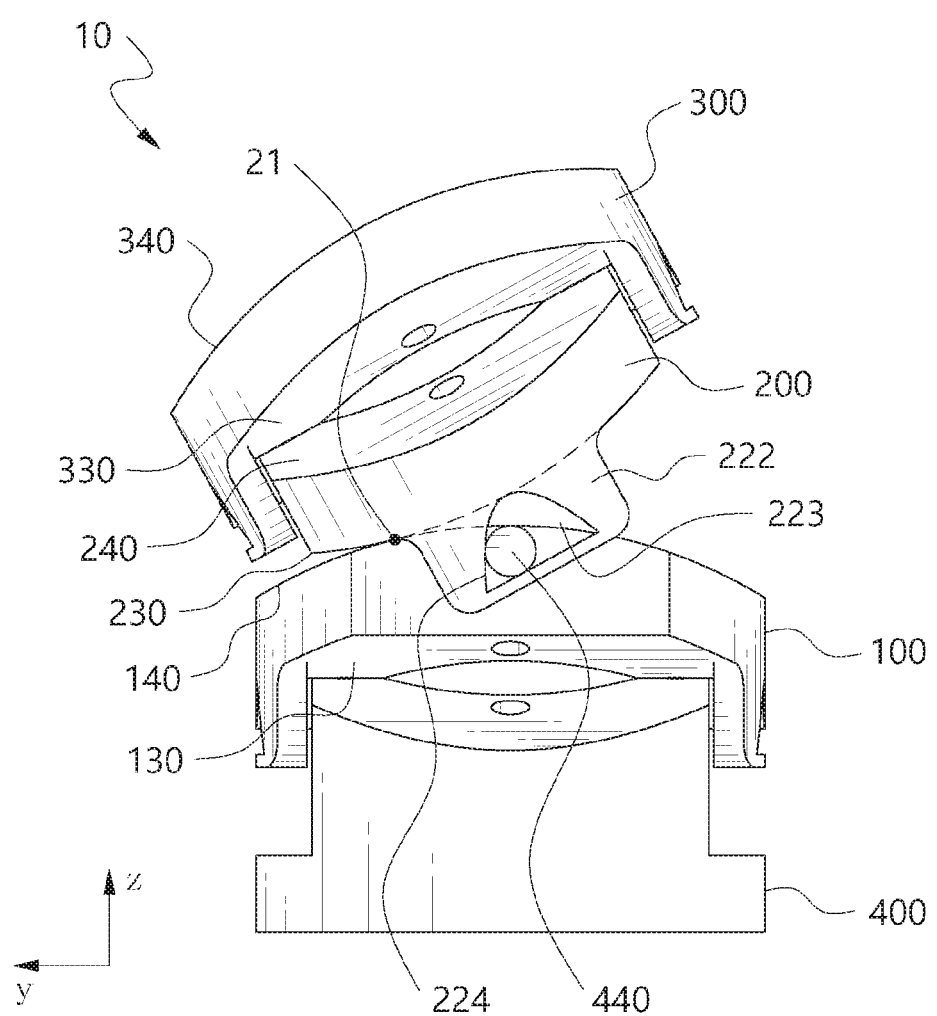
FIG. 7 is an operational state diagram of an articulating structure when viewed from a first direction.

FIG. 6 is a cross-sectional view of the articulating structure 10 when viewed in the first direction X, and FIG. 7 is an operational state diagram of the articulating structure 10 when viewed in the first direction X.

As shown in FIG. 6, in the initial state in which the articulating structure 10 is placed in a straight line, the second connection holes 162, 261, 362, 461 formed in each segment 100 to 400 are aligned in the lengthwise direction Z of the articulating structure 10, forming a substantially linear wire connection passage.

Each wire 510, 520 passes through the two second wire connection holes 162, 261, 362, 461 arranged in the second direction Y.

According to this embodiment, as the wire connection hole passes through the front and rear surfaces of the body of each segment, the wire is not exposed to the outside of the articulating structure 10 (the tube insert device 1) and is hidden inside. Accordingly, it is possible to avoid the interference of the wire with many tissues in the body. Moreover, it is possible to reduce the diameter of the articulating structure 10.

As shown in FIG. 6, for example, the front end of the wires 510, 520 is connected to a head 500 having a larger diameter than the second wire connection hole, and the head 500 is attached to the third front rolling contact surface 340 of the third segment 300. In FIG. 7, the wire and the head are omitted.

The rear end of the wires 510, 520 passes through the articulating structure 10 and extends to the rear end of the tube 11 through the tube 11 (see FIG. 1). A wire driving means not shown is installed at the rear end of the tube 11, and the wires 510, 520 are connected to the wire driving means. The wire driving means works to pull or release each of the wires 510, 520 in the lengthwise direction Z of the articulating structure 10.

The wires 510, 520 are made of a material having some elasticity, and in the initial state, the wire driving means pulls the two wires 510, 520 with equal tension. Accordingly, a force is applied to the articulating structure 10 rearwards symmetrically in the second direction Y. The articulating structure 10 may be fixed to the initial state by the balanced tension of the two wires 510, 520.

To steer the articulating structure 10, for example, the wire driving means may increase the tension by pushing the first wire 510, and on the contrary, release the tension applied to the second wire 520.

Accordingly, the left direction of the second direction Y of the third segment 300 is pulled back by the head 500, and the head 500 pushes back the first to fourth segments 100 to 400.

In this instance, even though the head 500 pushes back the first to fourth segments 100 to 400, the second segment 200 and the third segment 300, and the first segment 100 and the fourth segment 400 in line contact along the second contact line 22 cannot make relative movements with respect to each other. In contrast, as shown in FIG. 7, the first segment 100 and the second segment 200 in line contact along the first contact line 21 are slanted leftward of the second direction Y. That is, bending occurs at the connection joint between the first segment 100 and the second segment 200, and the tip of the articulating structure 10 is steered in the second direction Y.

As described above, a tool connection hole is formed at the center of each segment, and a tool connection passage 570 through which a tool passes is formed by the tool connection holes. Various types of surgical instruments, for example, an endoscope camera, a lighting device and a surgical instrument, inserted from the rear end of the tube 11 may be exposed through the front surface of the distal segment 300 through the tool connection passage 570.

As described above, as the tip of the articulating structure 10 is steered in the second direction Y, the surgical instrument may be steered in the second direction Y.

When the wire driving means increases the tension by pulling the second wire 520 while releasing the tension applied to the first wire 510, the first contact line 21 of the first segment 100 and the second segment 200 moves to the center as in the initial state, and the articulating structure 10 steered leftward of the second direction Y may return to the initial state. Further, when the wire driving means keeps pulling the second wire 520 while releasing the tension applied to the first wire 510, the articulating structure 10 may be steered rightward of the second direction Y that is opposite to FIG. 7.

Meanwhile, as described above, according to this embodiment, during rolling movements, the pin 150 of the first segment 100 may make relative position movements in the widthwise direction of the coupling hole 223 from the vertex 225 within the coupling hole 223 of the second segment 200. Accordingly, although not clearly shown, according to this embodiment, as the first segment 100 and the second segment 200 are slanted, the opposing openings of the second wire connection holes 162, 261 of the two segments disposed closer to each other are in substantial contact with each other. That is, the opposing openings of the second wire connection holes 162, 261 of the two segments 100, 200 are not significantly misaligned in the second direction Y, and they are substantially connected to each other. Accordingly, the wire connection passage maintains its unbent shape, thereby preventing a so-called "caught" wire phenomenon when steering.

Figure 8:
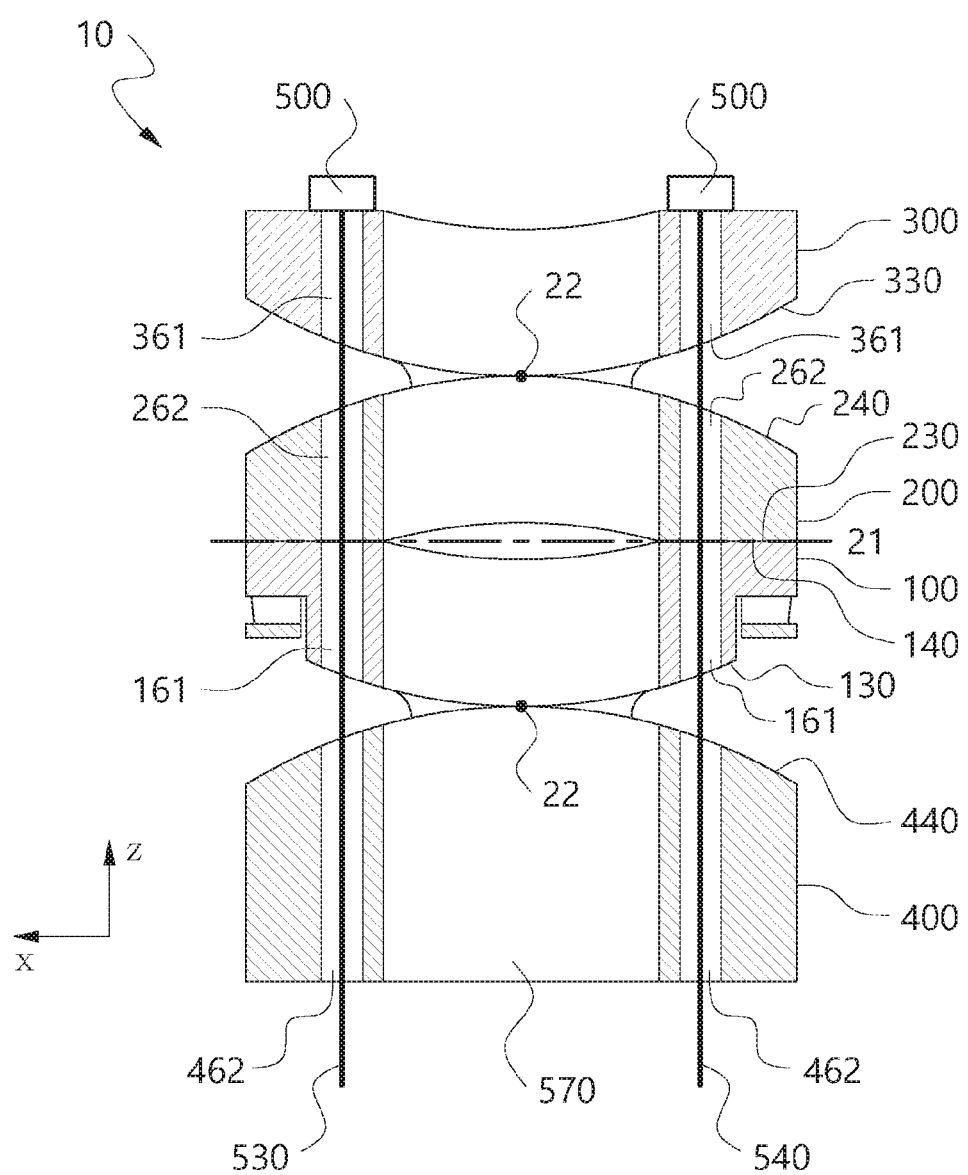
FIG. 8 is a cross-sectional view of an articulating structure when viewed from a second direction.
Figure 9:
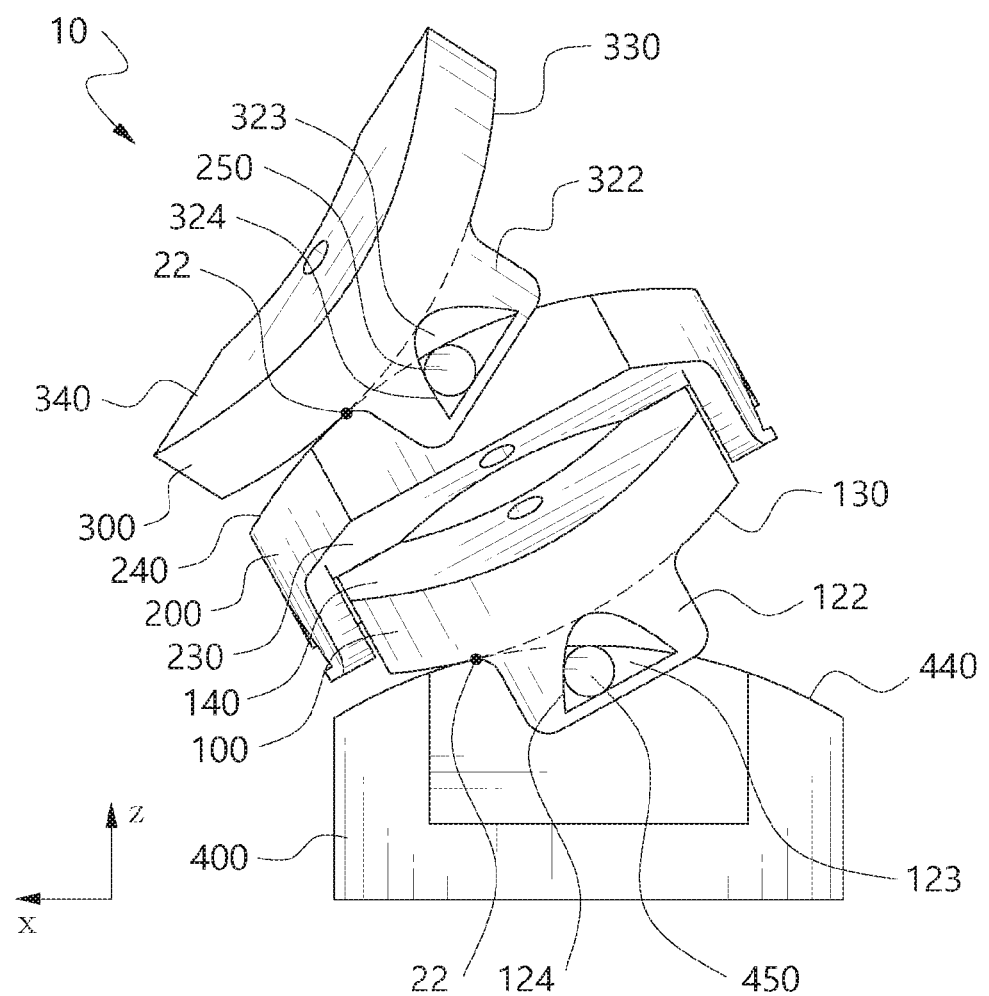
FIG. 9 is an operational state diagram of an articulating structure when viewed from a second direction.

FIG. 8 is a cross-sectional view of the articulating structure 10 when viewed in the second direction Y, and FIG. 9 is an operational state diagram of the articulating structure 10 when viewed in the second direction Y.

As shown in FIG. 8, in the initial state in which the articulating structure 10 is placed in a straight line, the first wire connection holes 161, 262, 361, 462 formed in each segment 100 to 400 are also aligned in the lengthwise direction Z of the articulating structure 10, forming a substantially linear wire connection passage.

Each wire 530, 540 passes through the two first wire connection holes 161, 262, 361, 462 arranged in the first direction X.

As shown in FIG. 8, for example, the front end of the wires 530, 540 is connected to the head 500 having a larger diameter than the first wire connection hole, and the head 500 is attached to the third front rolling contact surface 340 of the third segment 300. In FIG. 9, the wire and the head are omitted.

Likewise, the rear end of the wires 530, 540 passes through the articulating structure 10 and extends to the rear end of the tube 11 through the tube 11 (see FIG. 1), and is connected to the wire driving means.

In the initial state, the wire driving means pulls the two wires 530, 540 with equal tension. Accordingly, a force is applied to the articulating structure 10 rearwards symmetrically in the first direction X. The articulating structure 10 may be fixed to the initial state by the balanced tension of the wires 530, 540.

To steer the articulating structure 10, for example, the wire driving means may increase the tension by pulling the third wire 530, and on the contrary, release the tension applied to the fourth wire 540.

Accordingly, the left direction of the first direction X of the third segment 300 is pulled back by the head 500, and the head 500 pushes back the first to fourth segments 100 to 400.

In this instance, even though the head 500 pushes back the first to fourth segments 100 to 400, the first segment 100 and the second segment 200 in line contact along the first contact line 21 cannot make relative movements with respect to each other. In contrast, as shown in FIG. 9, the second segment 200 and the third segment 300, and the first segment 100 and the fourth segment 400 in line contact along the second contact line 22 are slanted leftward of the first direction X. In detail, the first segment 100 and the second segment 200 are slanted with respect to the fourth segment 400, and the third segment 300 is further slanted with respect to the slanted second segment 200. That is, bending occurs at two connection joints between the second segment 200 and the third segment 300 and between the first segment 100 and the fourth segment 400, and the tip of the articulating structure 10 is steered in the first direction X. Accordingly, the surgical instrument exposed to the front side of the articulating structure 10 through the tool connection passage 570 may be steered in the first direction X.

When the wire driving means increases the tension by pulling the fourth wire 540 while releasing the tension applied to the third wire 530, the second contact line 22, namely, a connection line of the second segment 200 and the third segment 300, and the first segment 100 and the fourth segment 400 moves to the center as in the initial state, and the articulating structure 10 steered leftward of the first direction X may return to the initial state. Further, when the wire driving means keeps pulling the fourth wire 540 while releasing the tension applied to the third wire 530, the articulating structure 10 may be steered rightward of the first direction X that is opposite to FIG. 9.

In the same way as the foregoing, according to this embodiment, as the first segment 100 and the fourth segment 400 are slanted, the first wire connection holes 161, 462 of two segments disposed closer to each other are not significantly misaligned in the first direction X, and they are connected in substantial contact with each other. Additionally, as the second segment 200 and the third segment 300 are slanted, the first wire connection holes 263, 361 of two segments disposed closer to each other are not significantly misaligned in the first direction X, and they are connected in substantial contact with each other. Accordingly, it is possible to prevent a so-called "caught" phenomenon from occurring in the wire passing through the first wire connection hole.

Although the steering of the articulating structure 10 in the first direction X and the second direction Y is separately described in FIGS. 6 to 9, it will be understood that it is possible to steer the articulating structure 10 in the first direction X and the second direction Y at the same time when the wire driving means manipulates the first to fourth wires 510 to 540 at the same time. That is, it is possible to steer the tip of the articulating structure 10 3-dimensionally within the bending limit of the articulating structure 10.

The articulating structure 10 is independently steered in the first direction X and the second direction Y by the pair of wires arranged in the first direction X and the pair of wires arranged in the second direction Y respectively, thereby simplifying the computation for 3-dimensional composite direction control of the tip.

Although this embodiment designates a fourth segment, a first segment, a second segment and a third segment in the order of from proximal to distal of the articulating structure 10, it should be understood that the segment name is not intended to limit the designation of the first to third segments described in the appended claims.

For example, the segment 400, the segment 100, and the segment 200 arranged one after another from proximal may be a first segment, a second segment and a third segment respectively, and on the contrary, the segment 300, the segment 200 and the segment 100 arranged one after another from distal may be a first segment, a second segment and a third segment respectively. Additionally, the segment 200, the segment 100 and the segment 400 may be a first segment, a second segment and a third in the appended claims.

According to the articulating structure 10 of this embodiment, it is possible to increase the support between each segment using pin coupling, and achieve relative segment steering by rolling movements by the rolling contact surface without using pin coupling as a hinge, thereby maintaining the smooth steering advantage of rolling movements.

What is claimed is:

1. An articulating structure that is steered by relative movement of a plurality of segments connected in series, the articulating structure comprising:
   a first segment and a second segment arranged in contact with each other,
   wherein contact surfaces of the first segment and the second segment are rolling contact surfaces in line contact on a first direction contact line extending in a first direction,
   the first segment has a pin on a side,
   the second segment has a coupling hole into which the pin is inserted,
   the second segment make a relative rolling movement with respect to the first segment in a second direction perpendicular to the first direction during which the first direction contact line moves while maintaining the line contact, and
   the coupling hole is formed with a larger area than the pin to allow the pin to make a relative position movement within the coupling hole during the rolling movement.

2. The articulating structure according to claim 1, wherein the coupling hole is formed to allow the pin to be relatively far away from the contact surface of the second segment during the rolling movement.

3. The articulating structure according to claim 1, wherein the coupling hole includes an inner side where the pin makes a relative position movement while being in contact during the rolling movement, and
   the inner side includes an inner side formed at an angle such that a width of the coupling hole in the second direction increases as a distance from the rolling contact surface of the second segment increases.

4. The articulating structure according to claim 3, wherein the pin makes a position movement in contact with the inner side, and
   the inner side of the coupling hole is formed in a curved shape.

5. The articulating structure according to claim 1, wherein the pin is positioned close to an upper end portion of the side of the first segment.

6. The articulating structure according to claim 1, wherein the pin protrudes from the side of the first segment,
   the side of the first segment includes a curved part and a flat part along a circumferential direction of the side of the first segment,
   the flat part extends in the second direction, and
   the pin is formed in the flat part.

7. The articulating structure according to claim 6, wherein the curved part is formed as part of a circumference of a circular cylinder, and
   when a circumference of a perfect circular cylinder is defined by extending the curved part, a height of the pin does not go beyond the circumference of the perfect circular cylinder.

8. The articulating structure according to claim 6, wherein the second segment includes a flange extending toward the first segment and having the coupling hole, and
   the flange covers at least a portion of the flat part, and has an inner surface parallel to a surface of the flat part.

9. The articulating structure according to claim 1, wherein the entire rolling contact surface of the first segment and the second segment is formed as part of a circumference of a circular cylinder.

10. The articulating structure according to claim 1, wherein the articulating structure comprises a third segment positioned in contact with the second segment, contact surfaces of the second segment and the third segment are rolling contact surfaces in line contact with each other on a second direction contact line extending in the second direction, the second segment has a pin on a side, the third segment has a coupling hole into which the pin formed in the second segment is inserted, and the second segment and the third segment make a relative rolling movement during which the second direction contact line moves while maintaining the line contact.

11. The articulating structure according to claim 10, wherein the plurality of segments has a wire connection hole passing through each segment in a front-rear direction, when the articulating structure is placed in a straight line, a wire passes through the wire connection holes of each segment arranged such that the wire connection holes are aligned in a lengthwise direction of the articulating structure, and the plurality of segments makes the relative movement by pulling or releasing the wire in the lengthwise direction of the articulating structure.

12. The articulating structure according to claim 11, wherein the wire connection holes include a pair of first direction wire connection holes arranged in the first direction and a pair of second direction wire connection holes arranged in the second direction.

13. The articulating structure according to claim 12, wherein a tool connection hole passing through each segment in the front-rear direction is formed at a center of the plurality of segments.

14. A tube insert device, comprising:

an elongated tube; and the articulating structure according to claim 1, connected to a front end of the tube.

* * * * *